US010733728B2

(12) United States Patent
Abbasi et al.

(10) Patent No.: US 10,733,728 B2
(45) Date of Patent: Aug. 4, 2020

(54) DEVICE AND METHOD FOR AUTOMATION OF MEAN AXIS OF ROTATION (MAR) ANALYSIS

(71) Applicants: Mayar Abbasi, Pierrefonds (CA); Aslam Khan, Mississauga (CA)

(72) Inventors: Mayar Abbasi, Pierrefonds (CA); Aslam Khan, Mississauga (CA)

(73) Assignee: KKT International Ltd. (BB)

( * ) Notice: Subject to any disclaimer, the term of this patent is extended or adjusted under 35 U.S.C. 154(b) by 152 days.

(21) Appl. No.: 16/302,509

(22) PCT Filed: May 30, 2016

(86) PCT No.: PCT/IB2016/053179
§ 371 (c)(1),
(2) Date: Nov. 16, 2018

(87) PCT Pub. No.: WO2017/199068
PCT Pub. Date: Nov. 23, 2017

(65) Prior Publication Data
US 2019/0172201 A1    Jun. 6, 2019

Related U.S. Application Data

(60) Provisional application No. 62/339,017, filed on May 19, 2016.

(51) Int. Cl.
*G06K 9/00*     (2006.01)
*A61B 6/00*     (2006.01)
(Continued)

(52) U.S. Cl.
CPC .......... *G06T 7/0012* (2013.01); *A61B 5/1071* (2013.01); *A61B 5/4566* (2013.01);
(Continued)

(58) Field of Classification Search
USPC ....... 382/100, 103, 106, 128–133, 168, 173, 382/181, 199, 216, 219, 224, 254, 275,
(Continued)

(56) References Cited

U.S. PATENT DOCUMENTS 9,084,629 B1* 7/2015 Rosa .................. A61H 1/008
2007/0036264 A1* 2/2007 Beyrard ............. A61B 5/0073
378/19
(Continued)

OTHER PUBLICATIONS

WIPO, Canadian International Searching Authority, International Search Report dated Feb. 17, 2017, International Patent Application No. PCT/IB2016/053179, 4 Pages.
(Continued)

*Primary Examiner* — Seyed H Azarin
(74) *Attorney, Agent, or Firm* — Baumgartner Patent Law; Marc Baumgartner

(57) ABSTRACT

A computer readable storage medium for determining a normalized mean axis of rotation (MAR) of a cervical spine in a patient is provided, having stored thereon instructions executable by a processor to perform steps of providing a flexion trace and an extension trace of each of cervical spine vertebrae C2 to C7 by detecting a start position, drawing a line concurrently as the pointing device follows the margin from the start position to a finish position and detecting the finish position; superimposing the flexion trace on the extension trace; providing for a user to correct an error in a trace; determining a MAR datum; and normalizing the MAR datum.

18 Claims, 10 Drawing Sheets

Flexion View

(51) Int. Cl.
*G06T 7/00* (2017.01)
*A61B 5/107* (2006.01)
*A61B 5/00* (2006.01)
*G06F 3/0484* (2013.01)
*G06F 3/0486* (2013.01)
*G06T 11/20* (2006.01)
*G06T 11/60* (2006.01)
*G16H 50/50* (2018.01)

(52) U.S. Cl.
CPC ........ *G06F 3/0486* (2013.01); *G06F 3/04845* (2013.01); *G06T 11/203* (2013.01); *G06T 11/60* (2013.01); *G06T 2207/30012* (2013.01); *G16H 50/50* (2018.01)

(58) Field of Classification Search
USPC ........ 382/276, 286, 305; 601/48; 378/19, 20
See application file for complete search history.

(56) References Cited

U.S. PATENT DOCUMENTS

| | | | | |
|---|---|---|---|---|
| 2012/0184885 | A1* | 7/2012 | Khan | A61H 1/008 601/48 |
| 2017/0258428 | A1* | 9/2017 | Distler | A61B 6/035 |
| 2017/0259085 | A1* | 9/2017 | Bennett | A61N 5/1037 |

OTHER PUBLICATIONS

WIPO, Canadian International Searching Authority, Written Opinion of the International Searching Authority dated Feb. 17, 2017, International Patent Application No. PCT/IB2016/053179, 5 Pages.

Abbasi, Mayer (Aug. 10, 2013) Semi-Automation of Mean Axis of Rotation (MAR) Analysis. Retrieved from http://digitool.library.mcgill.ca/webclient/StreamGate?folder_id=O&dvs=I486736050681-670& usePidl =true&usePid2=true.

Levinshtein et al., "TurboPixels: Fast Superpixels Using Geometric Flows", IEEE Transactions on Pattern Analysis and Machine Intelligence ( vol. 31 , Issue: 12 , Dec. 2009 ).

Desmoulin et al., "Spinal Intervention Efficacy on Correcting Cervical Vertebral Axes of Rotation and the Resulting Improvements in Pain, Disability and Psychsocial Measures", Musculoskeletal Pain 20(1):31-40 • Dec. 2011.

Amevo et al., "Instantaneous axes of rotation of the typical cervical motion segments: a study in normal volunteers" , Clinical Biomechanics, vol. 6, Issue 2, May 1991, pp. 111-117.

Amevo et al., "Instantaneous axes of rotation of the typical cervical motion segments: II. optimization of technical errors", Clinical Biomechanics, vol. 6, Issue 1, Feb. 1991, pp. 38-46.

Amevo et al., "Instantaneous axes of rotation of the typical cervical motion segments: I. an empirical study of technical errors", Clin Biomech (Bristol, Avon). Feb. 1991;6(1):31-7. doi: 10.1016/0268-0033(91)90039-S.

Dvorak et al., "Functional radiographic diagnosis of the cervical spine: flexion/extension", Spine (Phila Pa 1976). Jul. 1988;13(7):748-55.

* cited by examiner

Flexion View

Extension View

EXTENSION TRACING —204   FLEXION TRACING —202

212
o - ext. position
• - flex. position
214

216
IAR

DEVICE AND METHOD FOR AUTOMATION OF MEAN AXIS OF ROTATION (MAR) ANALYSIS

CROSS REFERENCE TO RELATED APPLICATIONS

The present invention is filed under 35 U.S.C. § 371 as the U.S. national phase of International Application No. PCT/IB2016/053179, filed May 30, 2016, which designated the U.S. and claims the benefit of U.S. Provisional Application Ser. No. 62/339,017, filed May 19, 2016 and entitled DEVICE AND METHOD FOR AUTOMATION OF MEAN AXIS OF ROTATION (MAR) ANALYSIS, each of which is hereby incorporated in its entirety including all tables, figures, and claims.

FIELD

The present technology relates to a method of assessing Mean Axis of Rotation (MAR) of the spinal vertebrae. More specifically, the technology is a semi-automated method that utilizes computer vision to assist in determining the MAR.

BACKGROUND

Over the years, technologies such as X-rays, Magnetic Resonance Imaging (MRIs) and other imaging technologies have been assisting doctors to assess and treat many types of health problems. However, for neck and back pain, it is often not possible to detect or correctly diagnose back pain simply by looking at patient X-rays. Often, patients report severe symptoms, but no apparent problems are found in the X-ray. Spine researchers have therefore explored more sophisticated methods to accurately diagnose spine related pain. Using the Mean Axis of Rotation (MAR) Analysis, which involves analyzing the cervical spine X-rays of a patient in extension and flexion positions, Mayer et al [1], linked patient symptoms to abnormal Mean Axis of Rotation (MAR) placement. Other studies also showed that MAR is a reliable measure for spine pathology in neck pain. However, Amevo et al [2] noted that different observers found the same mean location for the instantaneous axis at each segment in a test population of 17 normal subjects, but for any given subject the inter-observer and intra-observer differences were large, with a relative variation of up to 35%. Thus, while reliable for determining the mean location of the instantaneous axis of rotation in a population, the technique was not reliable for determining the axis in a given subject.

Amevo et al [3] modified the protocol. The reliability of a modified protocol for plotting the instantaneous axes of sagittal rotation for the cervical spine was evaluated by measuring the observer differences when the process was performed separately by two observers, and by a single observer, on two separate occasions. Small observer differences were found both for individual steps in the process and for the process as a whole. These differences were substantially less than those found using the conventional technique for plotting the instantaneous axes of rotation. The improvement in the technique was resultant from the use of stricter criteria for recognizing and tracing vertebral landmarks.

Amevo et al [4] then determined the locations of the instantaneous axes of rotation for the cervical motion segments C2 3 to C6 from flexion extension radiographs of 40 normal subjects using a modified overlay technique. The biological variation of the instantaneous axes of rotation was small, as was the technical error associated with the technique used. The data obtained enabled the formal definition of the normal range of locations for the instantaneous axes of rotation of the typical cervical motion segments.

In 2012, Desmoulin et al [5] used the MAR Analysis to demonstrate the success of Khan Kinetic Treatment (KKT), a non-invasive spine treatment for treating neck pain and back pain. It has been shown to do this by correcting the vertebral axis of rotation (alignment of the spine), as well as upregulating the genes within the discs, to give long term spinal health.

MAR is determined by analyzing the trajectory of cervical vertebrae as the patient moves from an extension position to a flexion position. To analyze the trajectory of vertebrae, each vertebra is traced in both positions, as shown in FIG. 1. For each pair of adjacent vertebrae, the upper vertebra moves along a circular trajectory relative to the lower vertebra, as shown in FIG. 1. The trajectory can be considered as a rotation about a specific axis of rotation. The axis of rotation can be calculated geometrically by first marking the translation vectors of 4 random points around the upper vertebra, from the extension position to the flexion position, with the lower vertebra fixed in space.

By bisecting the 4 translation vectors, the point of intersection of the bisecting lines represents the axis of rotation of the upper vertebra, as shown in FIG. 2. The location of the axis of rotation for a specific vertebra lies somewhere within or close to the vertebra below it. By placing a coordinate system about the bottom left corner of the lower vertebra, an (x,y) coordinate point can be assigned to the axis of rotation point, as shown in FIG. 3. This (x,y) coordinate point represents the MAR for the pair of adjacent vertebrae.

The steps to determine MAR manually are as follows:

Step 1 Trace: Manually trace C7 C2 vertebra on extension and flexion radiographs on acetate paper;

Step 2 Trace quality control: Compare each vertebra from the extension X-ray to the corresponding vertebrae in the flexion X-ray by superimposing the traces manually. The trace errors are manually identified and the average of the two traces is calculated and used for the remaining procedure;

Step 3 Calculate the MAR: Perform geometrical analysis to determine the movement of C2 C6 from Extension to Flexion, with respect to the adjacent lower vertebra, as described above (maximally superimpose C6 flexion trace with extension trace, mark four reference points on the four corners of the vertebra, overlap C7 of the flexion trace with C7 of the extension trace and mark new location of C6 reference point, then repeat for C2 to C5. Determine the MAR as described above); and Step 4 Normalization: In order to use the MAR for comparative diagnosis, it is important to define the location of the MAR of a vertebrae pair by its position relative to the lower vertebra. To do this, a coordinate system is first placed with its origin around the lower vertebra, after which the location of the MAR can be expressed as a coordinate within this system. For example, in the case of the MAR for C6 C7, the coordinate system would be placed around the C7 vertebra. To allow comparison of MAR values across patients with different size vertebra, it is also important to represent the location of the MAR relative to the total size of the vertebra. To do this, the x coordinate of the MAR is normalized against the width of the vertebra, where the x coordinate will equal 1 if the x value of the MAR falls exactly on the right border of the vertebra. Similarly, the y coordinate of the MAR is normalized against the height of the vertebra, where the y coordinate will equal 1 if the y value of the MAR falls exactly on the top border of the vertebra. The MAR Normalization step will be required to normalize the MAR for each pair of vertebrae in the cervical spine, from C2 C3 pair to the C6 C7 pair.

Note that the exact placement of the coordinate system, as well as the placement of the top and left boundaries of the vertebra, requires qualitative judgment by the user, as the shapes of the vertebrae vary. Detailed instructions on how to place the coordinate system are provided in [5]. This step is performed manually. The final MAR coordinate can be classified according to the definition in [4].

While MAR Analysis promises to help the medical community diagnose patient conditions much more accurately than before, a major obstacle in its wide clinical use lies in the substantial effort (2 to 3 hours) required to perform the analysis accurately. Initially, the MAR procedure was completely manual, performed using tracing paper and manual geometric calculations. It was then semi-automated. The user would click on points around the border of each vertebra to provide a collection of points. The processor would then connect the points with straight lines between the points. For each vertebra in each X-ray, the collection of points and the lines therebetween defined a trace. In general, about 30 to about 60 clicks were used to define a trace. Higher resolution images required proportionally higher number of clicks. For a 2560*3072 pixel image, it required, on average, 200 clicks to adequately trace a single vertebra. If the user clicked on fewer points, the accuracy of the trace was compromised. This approach is tedious, time consuming and subject to significant error. Further, the data were collected and stored as integers, thus the data were inherently inaccurate and lacking precision. In order to programme for tracing by clicking, the code goes into a "Wait for Event" state. When the user clicked on the image (Mouse Click Event), an event was triggered, resulting in a point on the screen. The code then returned to the "Wait for Event" state and waited for the next event. Hence, the user needed to "trigger an event" for each point by clicking the mouse on the image.

As discussed, to calculate the MAR for a pair of vertebrae, the movement of the upper vertebra from extension to flexion is measured. This measurement is achieved by marking 4 points around the vertebra, and determining the displacement of each point from extension to flexion. The remaining MAR calculations are based on the displacement of these 4 points. In the Semi-Automated MAR Analysis tool, the 4 corners of the box bounding the collection of pixels representing the moving vertebra were used as the 4 points required for the MAR calculation. However, as these were points on an image, they were represented as a pair of integers, one for the X location, and one for the Y location of the point. The precision of an integer is 1, as there are no decimals. So, by calculating the MAR based on graphical points on the image, all of the data points were being rounded to the nearest 1, causing a loss of precision in the calculation.

Also, the MAR tool calculated an average trace by using NCC Pattern Matching to overlay the extension trace on the flexion trace. However, the best match found by the NCC Pattern Matching algorithm may not actually have been the correct match in reality. Recall that NCC is working only with binary images, whereas the real image is the actual X-Ray. It is possible that 2 different matches had the same "best match" score in the NCC algorithm, whereas only one of the matches worked on the actual image.

There have been a number of attempts to automate reading of medical images. For example, in U.S. Pat. No. 8,050,473 an improved method of segmenting medical images includes aspects of live wire and active shape models to determine the most likely segmentation given a shape distribution that satisfies boundary location constrains on an item of interest is provided. The method includes a supervised learning portion to train and learn new types of shape instances and a segmentation portion to use the learned model to segment new target images containing instances of the shape. The segmentation portion includes an automated search for an appropriate shape and deformation of the shape to establish a best oriented boundary for the object of interest on a medical image.

In U.S. Pat. No. 8,081,811 a method, apparatus, and program for judging image recognition results, and computer readable medium having the program stored therein is provided to obtain more accurate image recognition results while alleviating the burden on the user to check the image recognition results. An image recognition unit recognizes a predetermined structure in an image representing a subject, then a recognition result judging unit measures the predetermined structure on the image recognized by the image recognition unit to obtain a predetermined anatomical measurement value of the predetermined structure, automatically judges whether or not the anatomical measurement value falls within a predetermined standard range, and, if it is outside of the range, judges the image recognition result to be incorrect.

The objective of the present technology is to use computer vision techniques to substantially reduce the effort required to calculate the MAR, while maintaining the scientific and clinical accuracy of the procedure. It would be of further advantage if a user could intervene in the analysis due to the difficulty in matching traces of each vertebrae on the Extensions and Flexion views. It would be of further advantage if there was an auto-adjust feature that would compensate for inter-user differences in analysis, especially in light of the capability of user intervention. It would be of advantage if the trace could be smooth without having to click a large number of dots. It would be advantageous if the data could be collected as double precision numbers (15-17 decimal places of precision). It would be of further advantage if the collected data could be stored as double precision numbers.

SUMMARY

An image analysis device for determining a normalized mean axis of rotation (MAR) of the cervical spine in a patient is provided that significantly reduces the time required for a user to determine the MAR, making this technique clinically viable. A user is able to intervene in the analysis in order to improve the accuracy of identification of the margins of the vertebrae as needed. There was an auto-adjust feature that can compensate for inter-user differences in analysis. The data can be collected as double precision numbers (15-17 decimal places of precision). By improving the storage capabilities the collected data can be stored as double precision numbers, and therefore analyzed as such as well. This greatly improves the accuracy.

Many causes of neck pain and disability cannot be readily diagnosed using standard imaging. Furthermore, many other spinal regions have been clinically correlated to the disturbances noted in the MAR of the cervical spine. MAR analysis has been shown to be very useful in diagnosing these cases, and tracking the effect of their treatment. A major hurdle in using MAR has been the time and man hours required for the analysis.

In one embodiment, an image analysis apparatus for determining a normalized mean axis of rotation (MAR) of a cervical spine of a patient using a flexion medical image and an extension medical image of each of cervical spine vertebrae two to seven (C2 to C7), is provided, the apparatus comprising:

an image output device configured to display the flexion medical image and the extension medical image; a pointing device configured to trace a margin of each of C2 to C7 vertebrae of the cervical spine; a processor, the processor in electronic communication with the pointing device; and a memory; the memory including instructions for the processor: to provide a flexion trace and an extension trace of C2 to C7 vertebrae by detecting a start position, drawing a line concurrently as the pointing device follows the margin from the start position to a finish position and to detect the finish position; to superimpose the flexion trace of a selected vertebra on the extension trace of the selected vertebra; to allow a user to correct an error in a trace; to determine the MAR; and to normalize the MAR.

In the apparatus, the pointing device may be a mouse to allow the user to click at the start position, drag along the margin of the vertebrae and release at the finish position to define each trace.

The apparatus may further comprise a screen in electronic communication with the processor, for displaying each trace.

In the apparatus, the image display device may be a Digital Imaging and Communications in Medicine (DICOM) viewer.

In the apparatus, the image display device may be a touch screen and the pointing device may be a pressure exerting device.

In the apparatus, the memory may be configured to instruct the processor to remove an erroneous segment of a trace in response to the user selecting the erroneous segment with the pointing device.

In the apparatus, the memory may be configured to instruct the processor to replace the erroneous segment of the trace in response to the user drawing a correct line with the pointing device.

In another embodiment, a computer readable storage medium for determining a normalized mean axis of rotation (MAR) of a cervical spine in a patient is provided, having stored thereon instructions executable by a processor to perform steps of providing a flexion trace and an extension trace of each of cervical spine vertebrae C2 to C7 by detecting a start position, drawing a line concurrently as the pointing device follows the margin from the start position to a finish position and detecting the finish position; superimposing the flexion trace on the extension trace; providing for a user to correct an error in a trace; determining a MAR datum; and normalizing the MAR datum.

The computer readable storage may further comprise instructions for prompting a user to define the trace.

The computer readable storage medium may further comprise instructions for prompting the user to rotate the vertebra prior to normalizing the MAR.

The computer readable storage medium may further comprise instructions to remove an erroneous segment of a trace in response to the user selecting the erroneous segment with the pointing device.

The computer readable storage may further comprise instructions to replace the erroneous segment of the trace in response to the user drawing a correct line with the pointing device.

The computer readable storage medium may further comprise look up tables for determining a standard range of MAR data.

The computer readable storage medium may further comprise instructions for judging whether or not the MAR datum falls within the standard range.

The computer readable storage medium may further comprise instructions for storing the datum as a double precision number.

In another embodiment, a semi-automated method of determining a MAR of a subject, using a flexion medical image and an extension medical image of each of cervical spine vertebrae C2 to C7 is provided, the method comprising: a user locating a pointing device on a start position of a selected image and moving the pointing device from the start position to a finish position along a margin of the vertebra and concomitantly, a processor drawing a line between the start position and the finish position; repeating the step to provide a flexion trace and an extension trace of each of cervical spine vertebrae C2 to C7; superimposing the flexion trace on the extension trace; determining a MAR datum; and normalizing the MAR datum.

The method may further comprise the user correcting an error in a trace.

In the method, correcting may include the user selecting an erroneous segment of a trace with the pointing device and the processor removing the erroneous segment.

In the method, correcting may include the user drawing a correct line with the pointing device and the processor replacing the erroneous segment.

FIGURES

DESCRIPTION

Figure 1B:
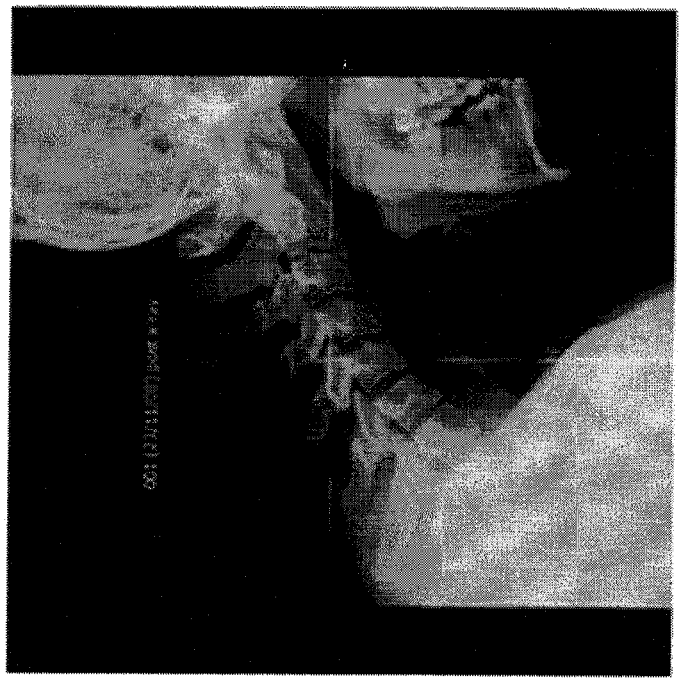
FIG. 1B shows a diagrammatic view of an X-ray showing the cervical vertebrae in extension.
Figure 1A:
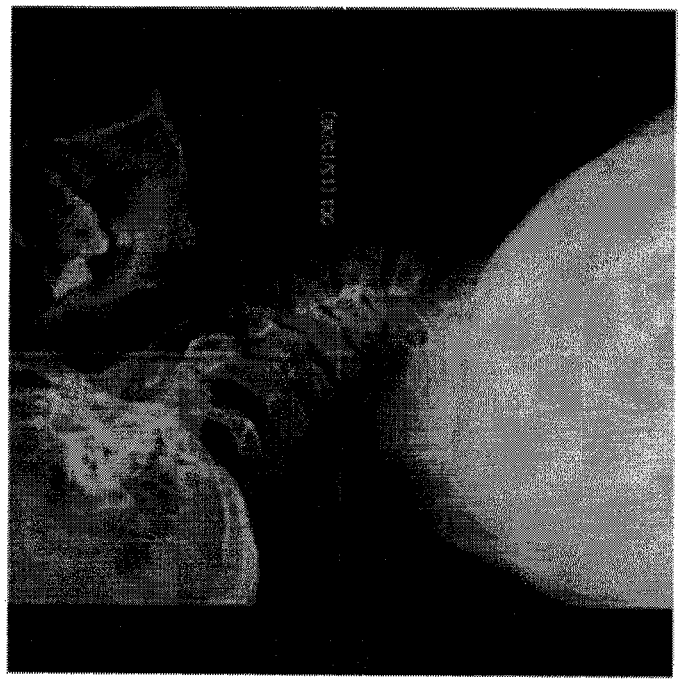
FIG. 1A shows a diagrammatic view of an X-ray showing the cervical vertebrae in flexion.
Figure 2:
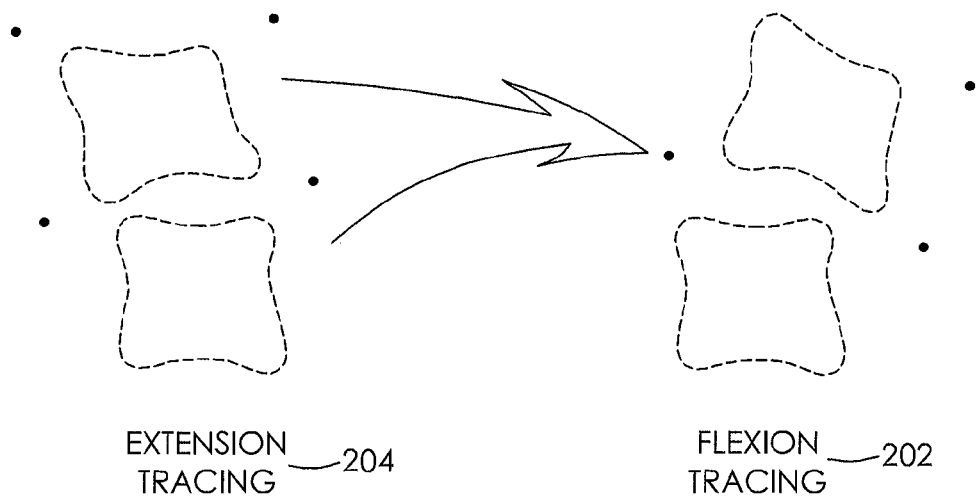
FIG. 2 is a prior art tracing showing a single pair of vertebrae in flexion and extension.

Except as otherwise expressly provided, the following rules of interpretation apply to this specification (written description, claims and drawings): (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, The terms "comprising," "having," "including," and "containing" are to be construed as open ended terms (i.e., meaning "including, but not limited to,") unless otherwise noted.

To the extent necessary to provide descriptive support, the subject matter and/or text of the appended claims is incorporated herein by reference in their entirety.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Definitions

Pointing device—In the context of the present technology, a pointing device is an input interface (specifically a human interface device) that allows a user to input spatial data to a computer. The pointing device allows a user to trace the margins of a vertebra in a smooth continuous action. A pointing device includes, but is not limited to a mouse, a joystick, and for use with a touch screen, a pen, a finger or other implement that can exert pressure on the touch screen.

Vertebra tracer—In the context of the present technology, a vertebra tracer is software that is retained in the memory to instruct the processor to provide a continuous trace from the "start position" to the "finish position".

Medical image—in the context of the present technology, a medical image is an X-ray, a nuclear magnetic resonance image (MRI), a Computerized (or computed) tomography CT scan or the like.

DETAILED DESCRIPTION

In one embodiment, a National Instruments Labview Development was used to develop the Semi-automated MAR Tool, which automates most of the steps as outlined below. The method is shown as a block diagram in FIG. 5.

Step 1: Trace: An image output device displays 8 digitized high resolution X-Ray images (2560*3072). The user is prompted 10 by the processor to trace each vertebra on each of the flexion and extension X-rays. The user manually traces the vertebra along the corticomedullary junction. The user holds the mouse button down 12 (this is the start position), and then slides 14 the mouse along the border of the vertebra. A line is drawn 16 along the path of the mouse, with points at every 3 pixels forming a continuous line as the mouse moves. This is especially beneficial for touch screen computers such as the Microsoft Surface®, where tracing the vertebra is done by using the Surface pen and tracing the vertebra.

Figure 5:
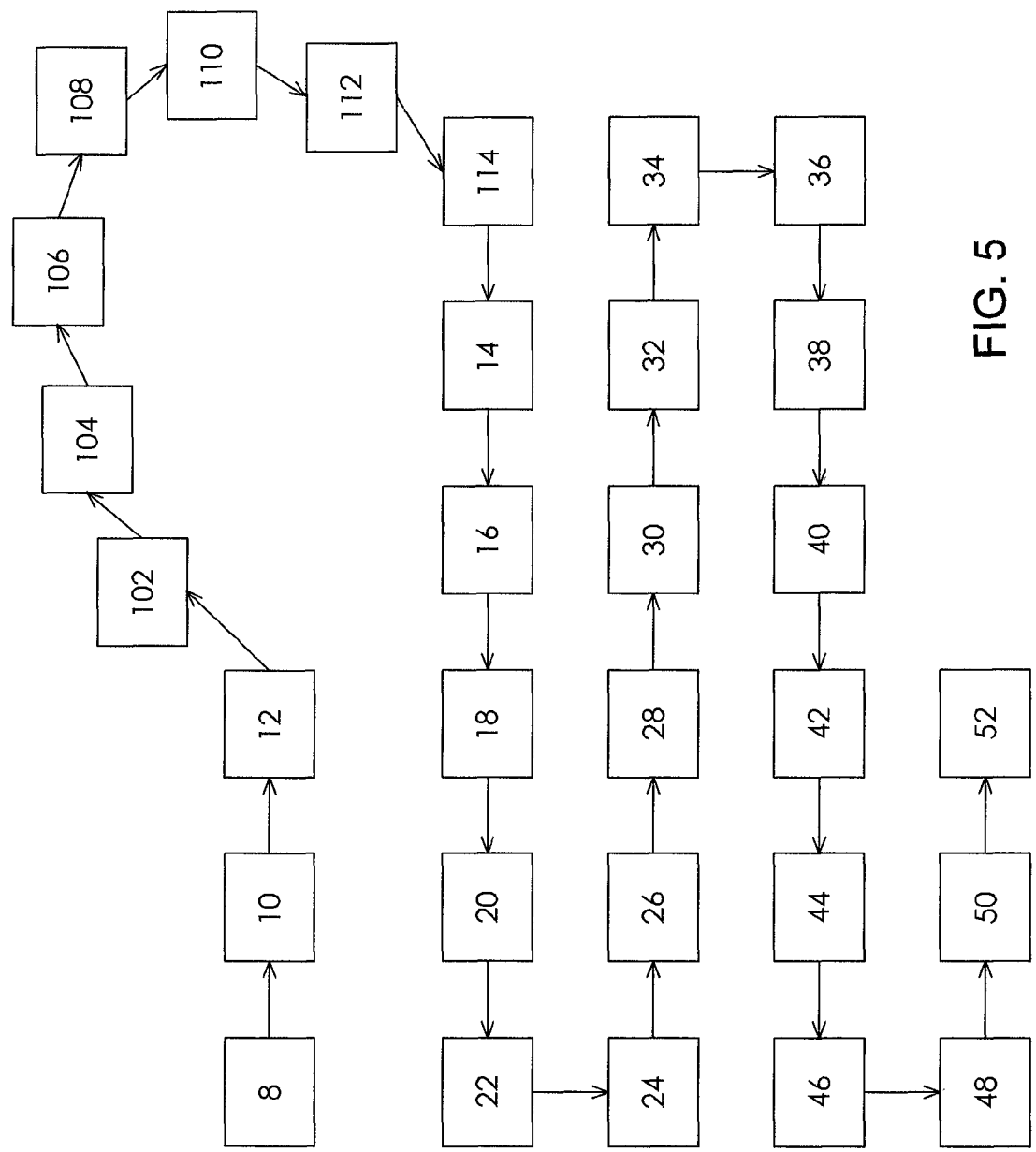
FIG. 5 is a block diagram of the method of the present technology.
Figure 6:
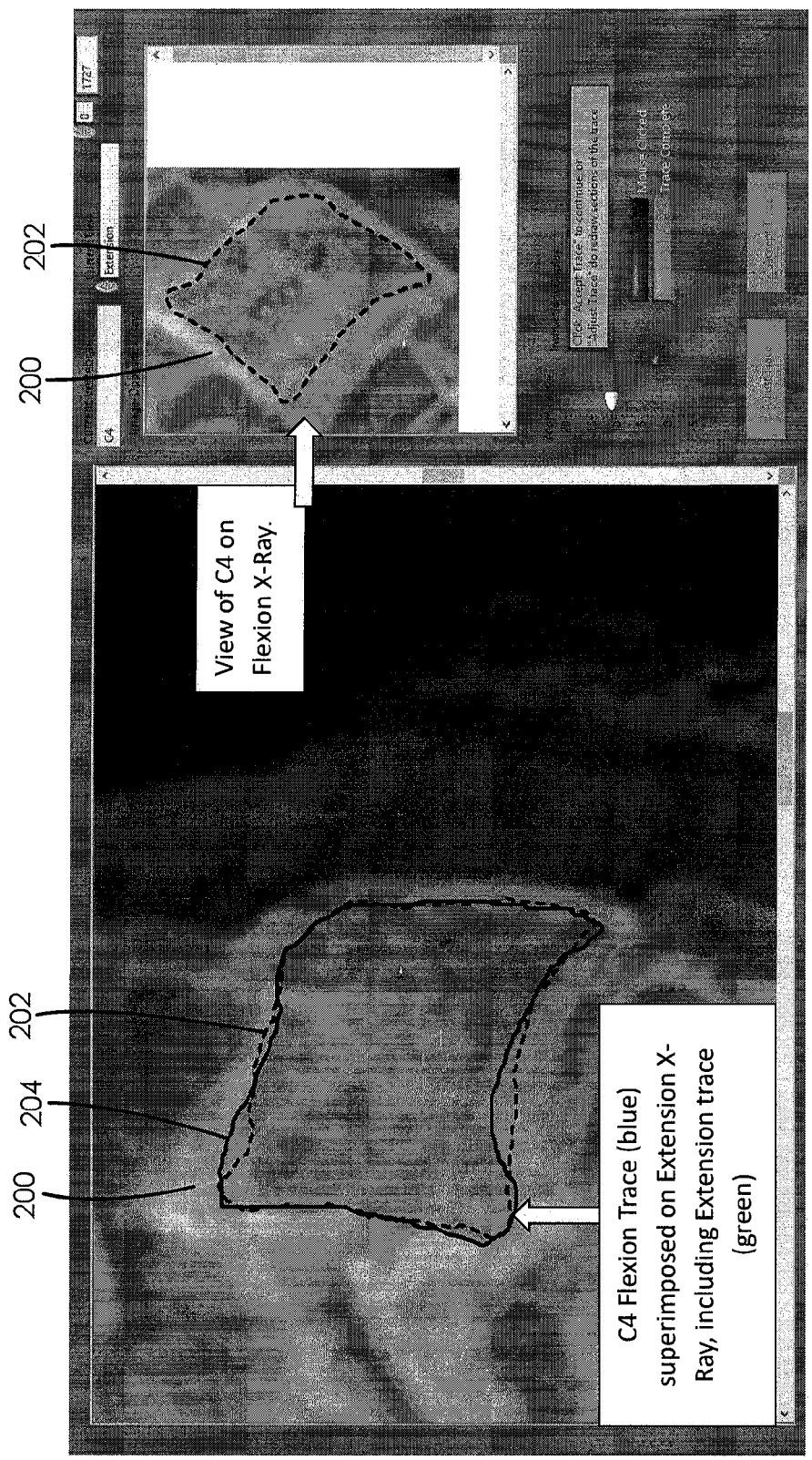
FIG. 6 shows the line drawing functionality of the present technology.

In order to use a touch screen and pen or to slide a mouse over the X-ray, the MAR tool was re-programmed as follows, as shown in FIGS. 5 and 6: When a mouse is clicked 102 (Mouse Click Event or start position), a dot is drawn 104. Instead of going back to the "Wait for Event" state after that, the code checks 106 if the mouse button is still pressed down. If it is, it checks 108 if the current mouse position moved (more than 3 pixels) from the last drawn point. If it has, it then draws a line 110 to another point. It continues looping until the mouse button is released 112 (finish position). Only after this time does the code go 114 into the "Wait for Event" state. This allows for natural drawing functionality. The memory therefore instructs the processor to determine when the mouse button is down and the mouse is moving, and to determine when the mouse button is no longer down. As long as the mouse button is down or the pen or other suitable pressure device is on the touch screen, the MAR tool will continue to draw a line. The line is drawn concurrently with the movement of the mouse or movement across the screen. The line follows the outline of the vertebra. This is unlike the prior art where each click resulted in a dot and then the dots were joined by straight line segments to approximate the outline of the vertebra.

Returning to FIG. 5, Step 2: Auto-adjust: As described above, the user manually traces the vertebra along the corticomedullary junction. The user's best efforts to place points exactly on the corticomedullary junction may still be subject to an error of 1 or 2 pixels. Computer Vision edge detection is used to detect 18 the best edge on the image, within a defined range from each trace point. For example, if the actual edge of the vertebrae on the image is 1 pixel north of the trace point, the auto-adjust feature can move this trace point north by 1 pixel. The same is repeated for all trace points.

This auto-adjust feature is helpful to compensate for inter-observer differences.

Step 3: Quality control algorithm and correction of traces: The process of superimposing the flexion traces on the extension traces and manually averaging the traces was replaced with the processor converting the traces into a binary pattern and using a Normalized Cross Correlation (NCC) based Pattern Matching algorithm to maximally superimpose the vertebra trace of the flexion position on the corresponding extension position, based on translation and rotation results of the pattern matching algorithm. To overcome the possible errors from the NCC pattern matching algorithm, the MAR tool allows user intervention at key moments of the Quality Control Algorithm, providing the user full control of the process.

Specifically, when the NCC pattern matching algorithm completes, it redraws the Extension trace and superimposes a rotated/translated Flexion trace. The user can observe the errors/differences of the Extension and Flexion traces on the X-ray. To correct these errors, the software provides the user a new interface which allows the user to mark the beginning and end of an erroneous segment on the trace (first on the Extension view, then on the Flexion view). The software then cuts out only this section of the trace, and allows the user to redraw just this section. This is highly advantageous for the following reasons:

1. The user does not need to redraw the whole trace, saving reducing the chance of introducing new errors; and
2. The user decides which segments are erroneous, by comparing the trace to the original X-Ray. Since the Extension trace is being compared to the Flexion trace, the error in the trace for any error segment can lie in either the Extension or the Flexion, and therefore should be corrected in the appropriate trace only. This interface allows the user to make the trace corrections only where required. In the previous version of MAR, the trace correction was done automatically by averaging the Extension and Flexion traces. However, doing so inadvertently introduced errors. For example, if in a certain trace segment, the Extension trace was correct (matched the original X-Ray), and the Flexion trace had 4 pixels of error, then the average trace (which goes between the Extension and Flexion trace) would have 2 pixels of error compared to the original X-Ray.

The step by step procedure follows.

Figure 7:
FIG. 7 shows the trace correction interface of the present technology.

FIG. 7 shows the trace correction interface, to correct the Extension trace. In this case, the Extension View of C4 is shown in the main window, and the Flexion View of C4 is shown in the upper right window.

One can observe that there was an error in the trace along the lower border of the trace, as the blue trace (Flexion trace superimposed on image) runs lower than the green trace (original Extension trace). The left and right borders are very accurately superimposed.

Figure 8:
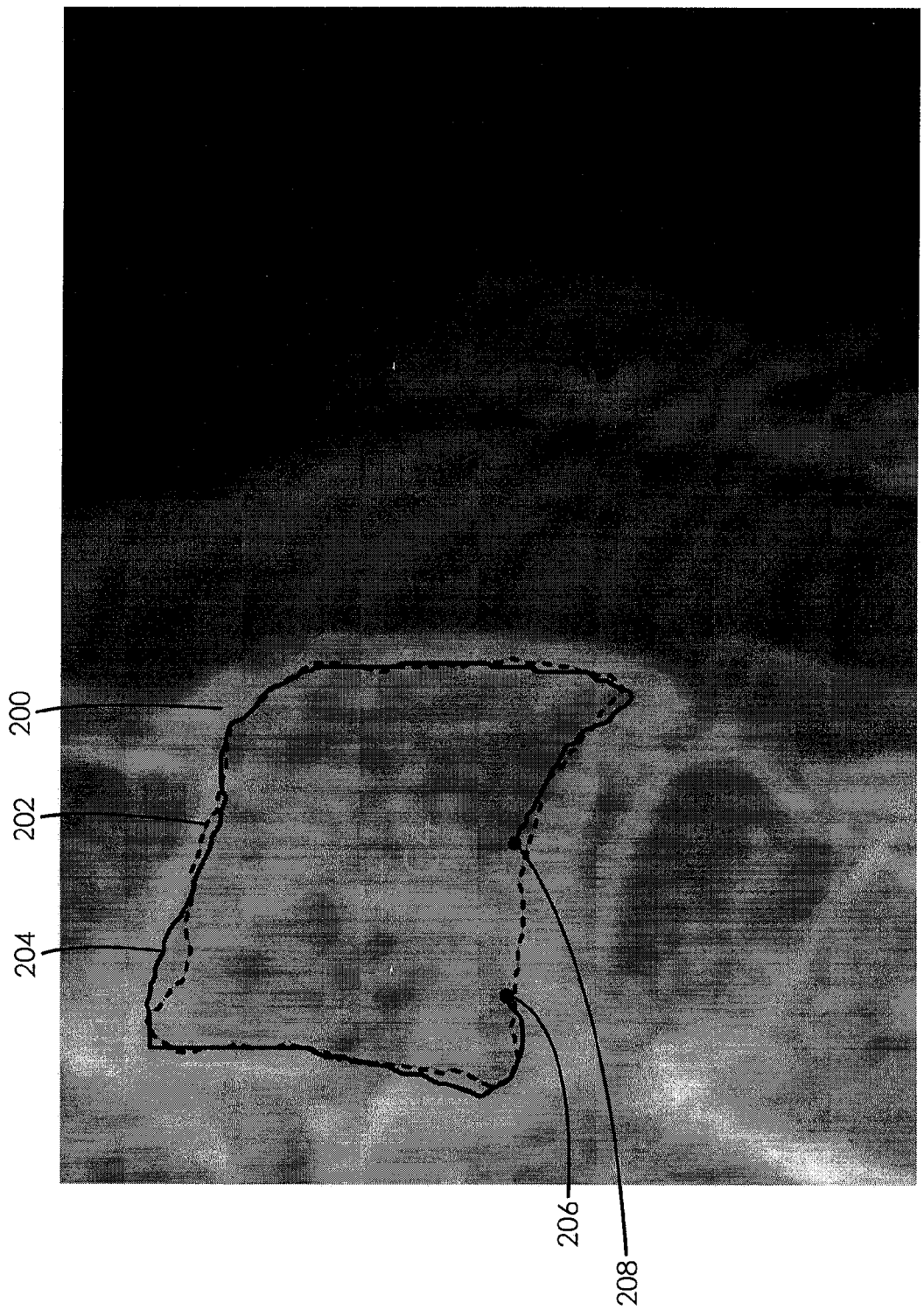
FIG. 8 shows identifying the segment to adjust in the trace correction interface of the present technology.

Identifying the Error:

At this point, the user decides 20 whether the extension trace is to be corrected, or the flexion trace is to be corrected. By observing the area where the traces are different in the Extension view, it was noticed 22 that the green trace line was following an area of the image where the border of the vertebrae is not so clear on the X-Ray (see FIG. 8). However, in the corresponding region on the Flexion X-ray (shown in the top right corner), the border of the vertebra on the X-Ray does appear more clearly. So, the user concluded 24 that the error is probably with the Extension Vertebra.

Figure 9:
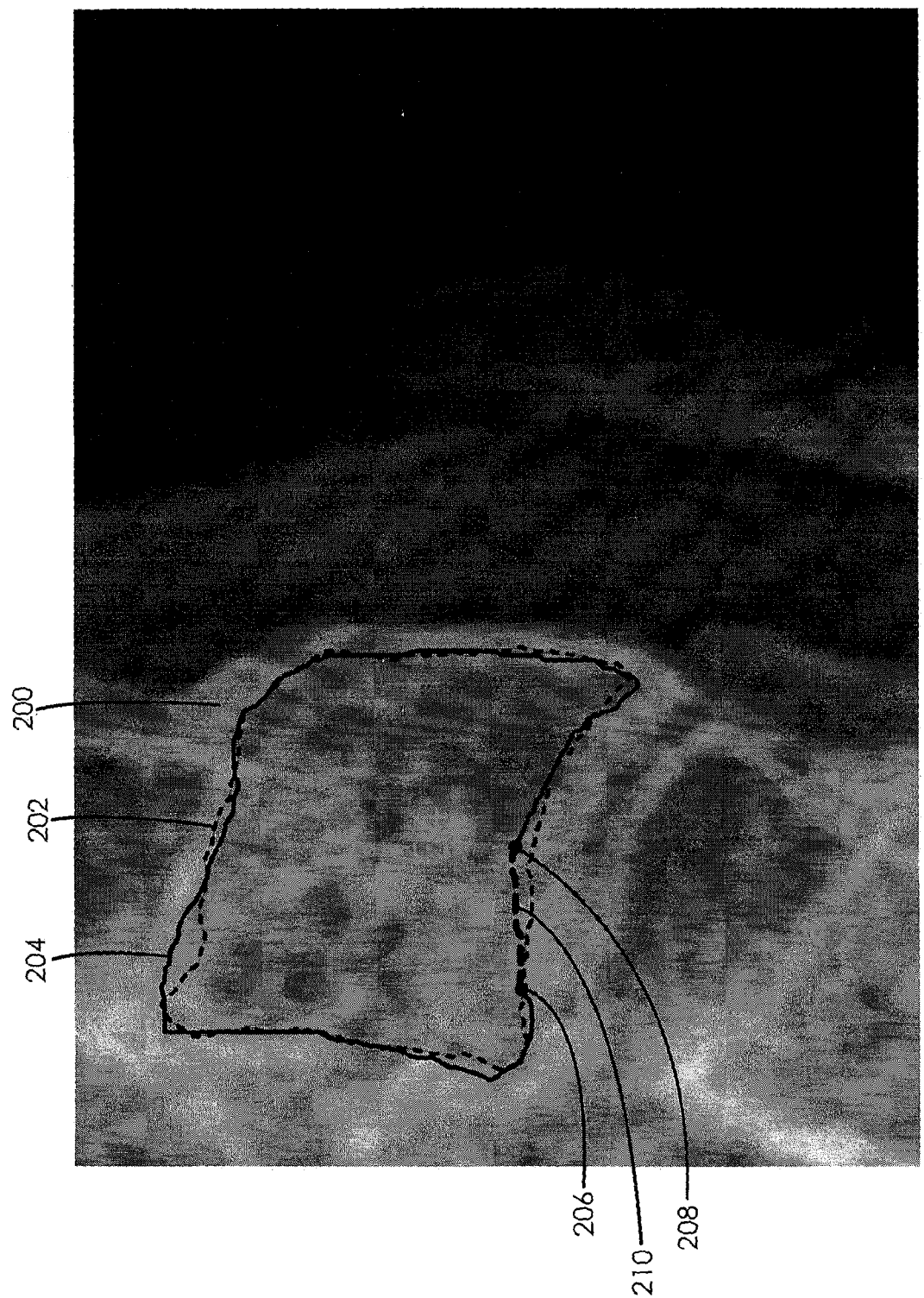
FIG. 9 shows cutting out of the segment to be adjusted in the trace correction interface of the present technology.
Figure 10:
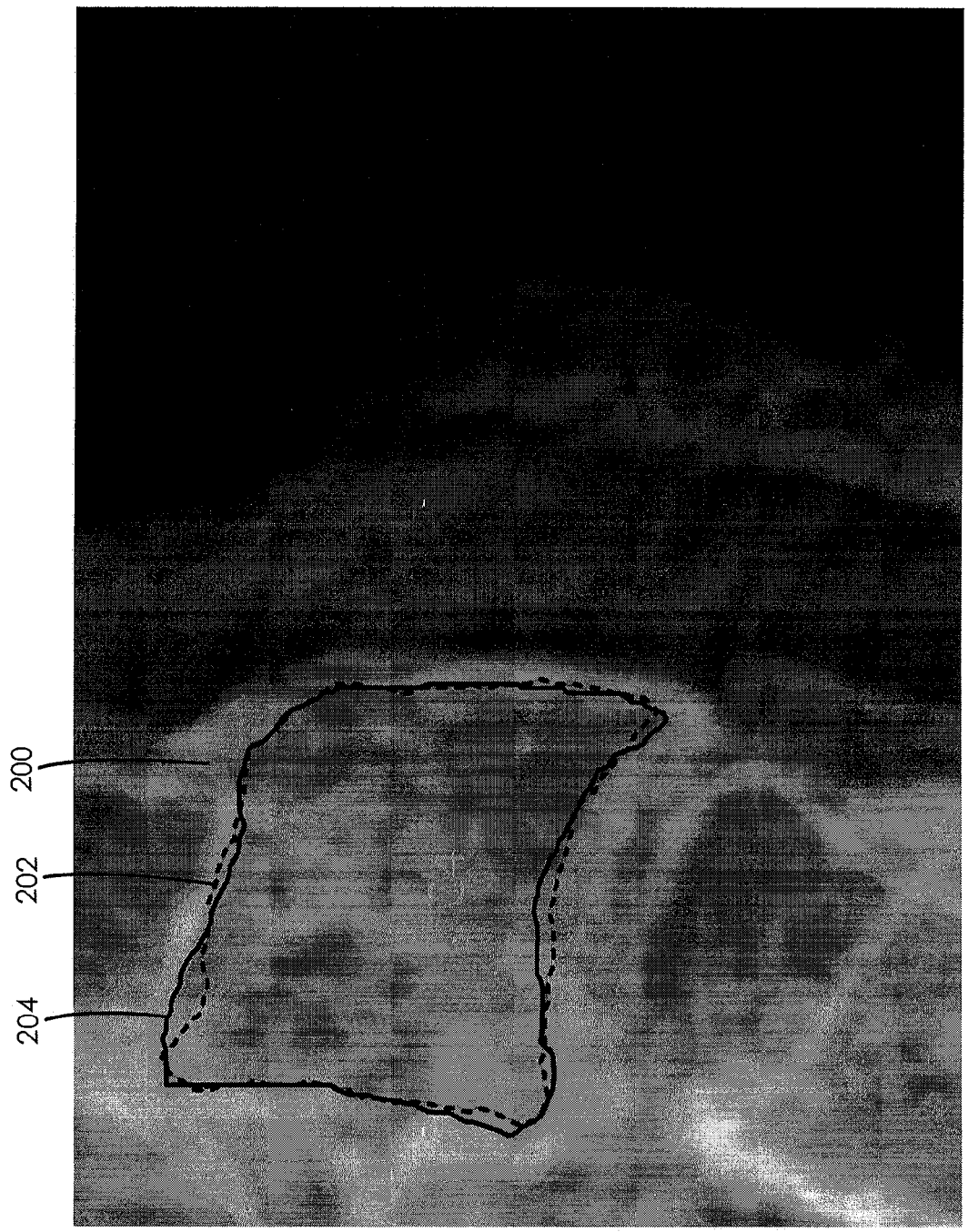
FIG. 10 shows redrawing of the segment to be adjusted in the trace correction interface of the present technology.
Figure 11:
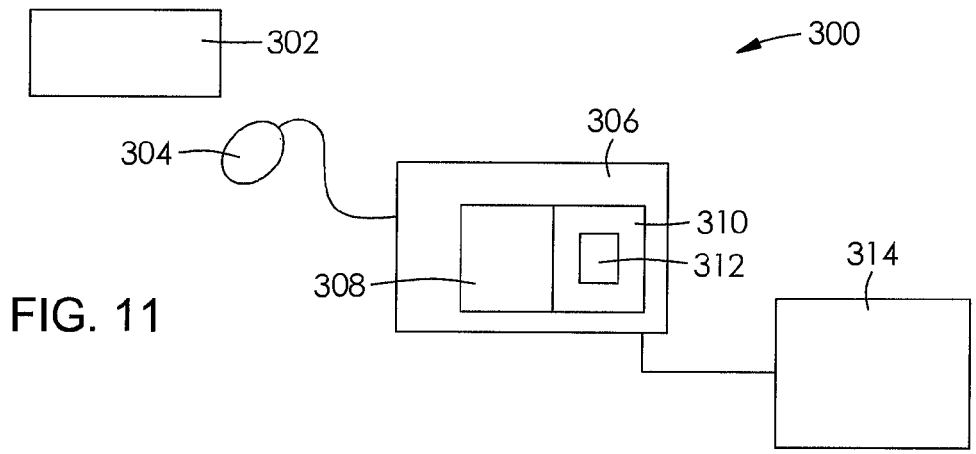
FIG. 11 is a schematic of the generalized apparatus for MAR analysis.

Correcting the Error:

After identifying that the error was in the Extension trace, the user corrected the error by adjusting the Extension trace. The MAR tool allowed the user to cut out (FIG. 9) 26 the erroneous segment, and redraw it (FIG. 10) 28 to provide 30 a corrected image (FIG. 11).

If the user determined that the error was on the flexion trace, then they would have accepted the Extension trace without making any adjustments to it. The next screen would provide a similar interface, except the Flexion view would be in the primary window, and the extension view in the smaller window.

Also note that often, some errors were corrected in each view.

After correcting the errors in the trace, the Quality Control algorithm continues as before, providing 32 match scores for the all the updated traces. The user continued this process until he/she was satisfied with the scores.

Step 4—Calculating the MAR: NCC Pattern Matching is again used by the processor to overlay 34 the corresponding averaged traces, and geometric calculations are performed to calculate 36 the MAR. More specifically, the 4 corners of the bounding box of each vertebrae trace are used as the reference points. Since the translation/rotation of the corresponding vertebrae is known from the previous step, the same translation/rotation to the 4 reference points of the adjacent vertebrae is applied to determine the relative movement. Geometry is used to calculate the equation of the 4 bisecting lines, which is then used to find their intersection to give the absolute MAR coordinates. The MAR Tool allows parallel processing of the Quality control algorithm. After the user completes tracing the vertebrae on the Extension view, the MAR Tool performs at least part of the Quality control algorithm in the background while the user traces the Flexion views.

Figure 3:
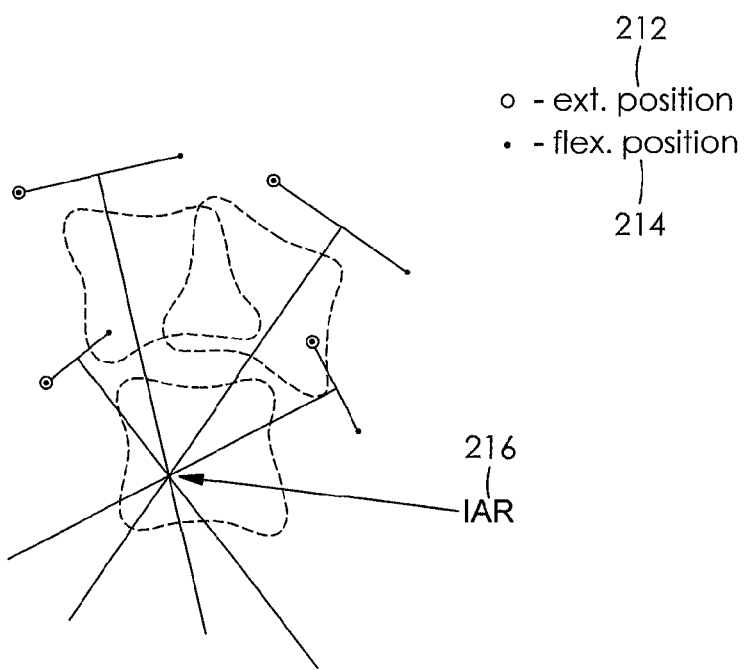
FIG. 3 is a prior art geometric analysis to determine MAR manually.
Figure 4:
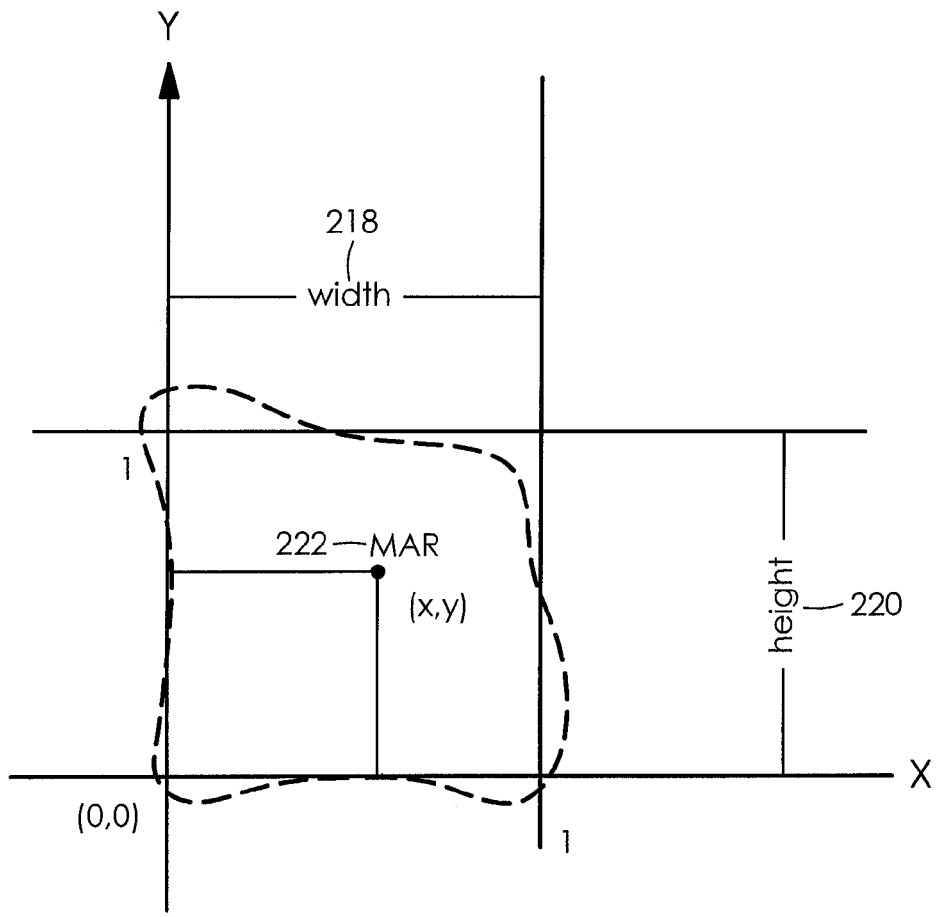
FIG. 4 is a prior art coordinate system placed on vertebrae for manual MAR determination.

Step 5—Normalization: The Normalization step involves placing an x y coordinate system about each vertebra to define a rectangular trapezoid equivalent of the vertebra. Since the vertebrae in the X-rays may be "diagonal" in space due to the position of the patient, the trace of the vertebrae also initially depicts the vertebrae in a diagonal manner. Therefore, before placing an x y coordinate system on the vertebra, it is first necessary to rotate 38 the vertebrae until the orientation of its base is horizontal (as shown in FIG. 3). When the orientation of the vertebra is correct, the user presses 40 the 'Set Grid' button, which provides the user a floating horizontal line, which is placed along the base of the vertebra to define the x axis. Once the horizontal line is placed, a floating vertical line representing the y axis is provided 42 to the user, which is placed along the left side of the vertebra to define the y axis. Similarly, after the y axis is placed, then another horizontal line is provided 44, which is placed along the top of the vertebra to define its height. Finally, after placing that line, another vertical line is provided 46 to the user which is placed along the right side of the vertebra, to define its width. This completes the definition of the rectangular trapezoid equivalent of the vertebra. The absolute MAR coordinate is then normalized 48 by representing the x coordinate location as a fraction of the total width, and the y coordinate location as a fraction of the total height. This normalization procedure is repeated for each of the vertebrae pairs to normalize all of the MAR.

Step 6—Storage, analysis and judging: The processor then stores 50 the data and analyzes 52 the data, using look up tables, to determine a standard range and to judge, using a MAR judging program, whether or not the calculated and normalized MAR falls within the standard range.

To prevent the loss of precision due to rounding the data into integers, the MAR tool stores all data as double precision numbers. All calculations were performed using these double precision numbers, with no rounding at any step.

In a second embodiment a mode for scalar images from Magnetic Resonance Imaging (MRI) and for Computerized tomography (CT) is provided. In this embodiment, tracing is effected using super voxels or using Turbo pixels. The remainder of the analysis is the same as for embodiment one.

In a third embodiment, Artificial Intelligence replaces the human user. All steps as outlined above are the same.

As shown in FIG. 11, a generalized schematic of the apparatus, generally referred to as 300 has an image output device 302 for displaying an X-ray, a pointing device 304 for a user to draw over the X-ray, a computing device in electronic communication with the pointing device 304 and generally referred to as 306, including a processor 308 under the control of a memory 310, the memory including the MAR tool 312 and a screen 314 in electronic communication with the computing device 306.

Figure 12:
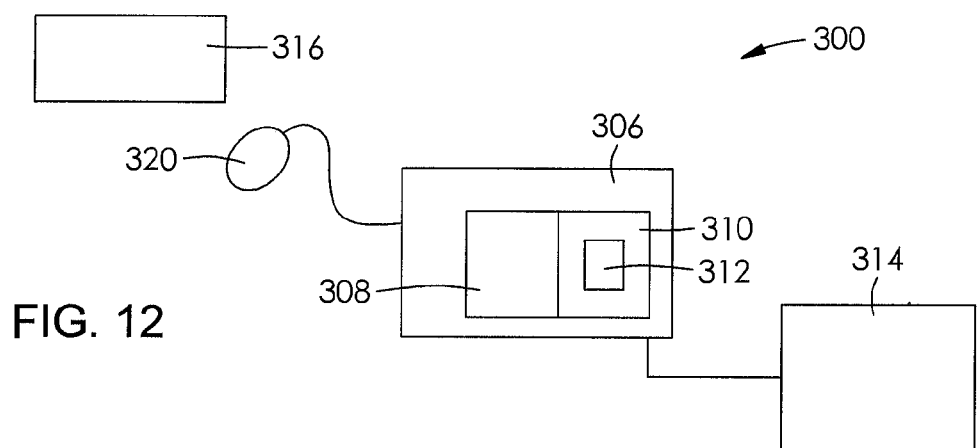
FIG. 12 is one embodiment of the apparatus of FIG. 11.

As shown in FIG. 12, the image output device 302 is a Digital Imaging and Communications in Medicine (DICOM) viewer 316 and the pointing device 304 is a mouse 320.

Figure 13:
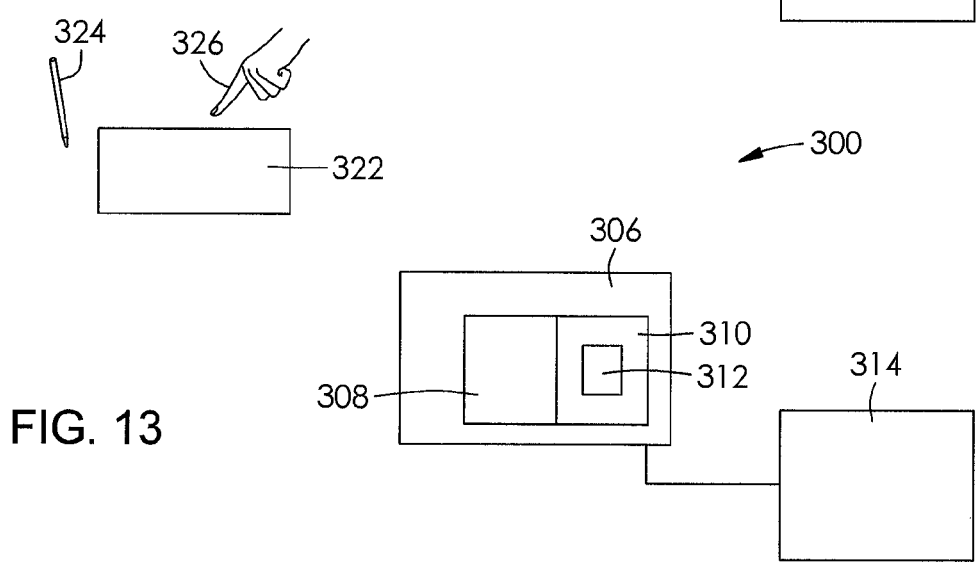
FIG. 13 is another embodiment of the apparatus of FIG. 11.

As shown in FIG. 13, the image output device 302 is a touch screen 322 and the pointing device 304 is a pen 324 or other pressure exerting device 326. In this embodiment, screen 314 may or may not be included as a separate component as the touch screen provides dual functionality as the image output device and the screen.

EXAMPLES

Example 1

The semi-automated MAR Tool for Turbo pixels will be used to provide traces of sets of CT images, showing the cervical vertebrae in flexion and in extension. The method will be controlled by Artificial Intelligence or a human user. It will be found that the accuracy of the tracing will be superior to that of the Turbo pixels method. The remainder of the steps will be the same as for the semi-automated mode.

Example 2

The semi-automated MAR Tool for super voxels will be used to provide traces of sets of MRI images, showing the cervical vertebrae in flexion and in extension. The method will be controlled by Artificial Intelligence or a human user. It will be found that the accuracy of the tracing will be superior to X-ray tracing. The remainder of the steps will be the same as for the semi-automated mode.

Example 3

The automated MAR Tool for super voxels will be used to provide traces of sets of CT images, showing the cervical vertebrae in flexion and in extension. The method will be controlled by Artificial Intelligence or a human user. It will be found that the accuracy of the tracing will be superior to X-ray tracing. The remainder of the steps will be the same as for the semi-automated mode.

Example 4

The automated MAR Tool for Turbo pixels will be used to provide traces of sets of MRI images, showing the cervical vertebrae in flexion and in extension. The method will be controlled by Artificial Intelligence or a human user. It will be found that the accuracy of the tracing will be superior to X-ray tracing. The remainder of the steps will be the same as for the semi-automated mode.

Example 5

An Artificial Intelligent (AI) MAR tool will use superpixels to perform an initial trace of the Extension and Flexion vertebra. AI will be used to perform high-level object detection to identify each vertebra in the Extension and Flexion X-Ray.

The Trace correction algorithm will then be executed, with the Extension trace of each vertebra superimposed on the Flexion trace (and vice versa). Trace differences and trace errors will become apparent after this superimposition.

To correct the error in the traces, AI edge detection will be used to automatically analyze the traces and compare them to the original X-Rays where errors are detected. AI (probabilistic reasoning or other) will be used to determine whether, for each erroneous segment, the source of the error is from the Extension trace or the Flexion Trace.

After identifying the source of the error, AI (edge detection, boundary detection, and boundary ownership) will be used correct the traces. This procedure will continue until the traces are satisfactory.

Once the traces are satisfactory, the MAR will be calculated as before.

Once the MAR is calculated, then AI will be used to perform the Normalization routine. The software will rotate the vertebra traces and evaluate the "flatness" of the vertebrae, until the optimal rotation is determined. The X axis and Y axis will then be placed on the optimal location of the vertebra, allowing the normalized MAR to be calculated.

Example 6

The Extension X-ray and Flexion X-ray represent the extreme positions of the vertebra in Extension-Flexion motion. The data will be used to graphically simulate the continuous movement of each vertebra. This graphical representation can be used to educate the public regarding MAR, and demonstrate normal vs abnormal movement. The data will also be used for three dimensional simulation of the Extension-Flexion movement. The three dimensional simulation will be printed with a three dimensional printer to produce a three dimensional model of a patient's cervical spine in each of the flexion and extension positions. The actual three dimensional shape of the vertebra can be simulated and a three dimensional model produced.

Example 7

The MAR data will be mined to gain an understanding and potentially correlate pathology with symptoms and predict future health problems.

Example 8

The MAR data will be used to improve diagnostics and to provide educational material.

The objective of this work was to use computer vision techniques to reduce the effort required perform the MAR analysis, while maintaining the scientific accuracy of the MAR. The execution results show that the effort was reduced from an average of 140 minutes for the Manual Mode, to less than 13 minutes for the previous Semi-automated mode and less than 10 minutes for the current semi-automated mode. The fully automated mode is expected to require less than 4 minutes for the Automated mode, a reduction of over 97% relative to the Manual mode and further improvement over the Semi-automated mode, therefore, of about 7%.

While example embodiments have been described in connection with what is presently considered to be an example of a possible most practical and/or suitable embodiment, it is to be understood that the descriptions are not to be limited to the disclosed embodiments, but on the contrary, is intended to cover various modifications and equivalent arrangements included within the spirit and scope of the example embodiment. Those skilled in the art will recognize, or be able to ascertain using no more than routine experimentation, many equivalents to the specific example embodiments specifically described herein. For example, other imaging techniques may be used, resulting in other images being analyzed. Such equivalents are intended to be encompassed in the scope of the claims, if appended hereto or subsequently filed.

REFERENCES CITED

[1] Mayer et al., "Functional radiographic diagnosis of the cervical spine: flexion/extension," Spine, vol. 13, pp. 748 755, 1988.
[2] Amevo et al., "Instantaneous axes of rotation of the typical cervical motion segments: I. an empirical study of technical errors," Clinical Biomechanics 1991; 6: 31 37.
[3] Amevo et al., "Instantaneous axes of rotation of the typical cervical motion segments: II. Optimization of technical errors," Clinical Biomechanics 1991: 6: 36 46.
[4] Amevo et al., "Instantaneous axes of rotation of the typical cervical motion segments: a study in normal volunteers," Clinical Biomechanics, no. 6, pp. 111 117, 1991.
[5] Desmoulin et al., "Spinal Intervention Efficacy on Correcting Cervical Vertebral Axes of Rotation and the Resulting Improvements in Pain, Disability and Psychosocial Measures," Journal of Musculoskeletal Pain, vol. 20, 2012.
[6] A. Levinshtein, "TurboPixels: Fast Superpixels Using Geometric Flows," IEEE Transactions on Pattern Analysis and Machine Intelligence, vol. 31, no. 12, p. 2290, 2009.

Tables:

TABLE 1

Parameters returned by Labview Vision Pattern Matching algorithm

| Parameter | Description |
|---|---|
| Position | (x, y) location of the center of the template |
| Angle | Degrees of rotation between the template and the pattern found |
| Scale | A ratio of the size difference between the template image and the found pattern |
| Score | A measure of the match between the template and the found pattern. Perfect match = 1000 |
| Bounding Box | An array of 4 (x, y) points defining the bounding box of the template |

The invention claimed is:

1. An image analysis apparatus for determining a normalized mean axis of rotation (MAR) of a cervical spine of a patient using a flexion medical image and an extension medical image of each of cervical spine vertebrae two to seven (C2 to C7), the apparatus comprising:
an image output device that is a Digital Imaging and Communications in Medicine (DICOM) viewer configured to display the flexion medical image and the extension medical image; a pointing device configured to trace a margin of each of C2 to C7 vertebrae of the cervical spine as a continuous line; a processor, the processor in electronic communication with the pointing device; and a memory; the memory including instructions for the processor: to provide a flexion trace and an extension trace of C2 to C7 vertebrae by detecting a start position, drawing a line concurrently as the pointing device follows the margin from the start position to a finish position and to detect the finish position; to superimpose the flexion trace of a selected vertebra on the extension trace of the selected vertebra; to allow a user to remove or correct an error in a trace; to determine the MAR; and to normalize the MAR.

2. The apparatus of claim 1, wherein the pointing device is a mouse to allow the user to click at the start position, drag along the margin of the vertebrae and release at the finish position to define each trace.

3. The apparatus of claim 2, further comprising a screen in electronic communication with the processor, for displaying each trace.

4. The apparatus of claim 1, wherein the image display device is a touch screen and the pointing device is a pressure exerting device.

5. The apparatus of claim 4, wherein the memory is configured to instruct the processor to remove an erroneous segment of a trace in response to the user selecting the erroneous segment with the pointing device.

6. The apparatus of claim 5, wherein the memory is configured to instruct the processor to replace the erroneous segment of the trace in response to the user drawing a correct line with the pointing device.

7. A non-transitory computer readable storage medium for determining a normalized mean axis of rotation (MAR) of a cervical spine in a patient, having stored thereon instructions executable by a processor to perform steps of providing a flexion trace and an extension trace on a Digital Imaging and Communications in Medicine (DICOM) viewer of each of cervical spine vertebrae C2 to C7 by detecting a start position, drawing a continuous line concurrently as the pointing device follows the margin from the start position to a finish position and detecting the finish position; superimposing the flexion trace on the extension trace; providing for a user to correct an error in a trace; determining a MAR datum; and normalizing the MAR datum.

8. The computer readable storage medium of claim 7, further comprising instructions for prompting a user to define the trace.

9. The computer readable storage medium of claim 8, further comprising instructions for prompting the user to rotate the vertebra prior to normalizing the MAR.

10. The computer readable storage medium of claim 9, further comprising instructions to remove an erroneous segment of a trace in response to the user selecting the erroneous segment with the pointing device.

11. The computer readable storage medium of claim 10, further comprising instructions to replace the erroneous segment of the trace in response to the user drawing a correct line with the pointing device.

12. The computer readable storage medium of claim 11, further comprising look up tables for determining a standard range of MAR data.

13. The computer readable storage medium of claim 12, further comprising instructions for judging whether or not the MAR datum falls within the standard range.

14. The computer readable storage medium of claim 13, further comprising instructions for storing the datum as a double precision number.

15. A semi-automated method of determining a MAR (mean axis of rotation) of a subject, using a flexion medical image and an extension medical image displayed on a Digital Imaging and Communications in Medicine (DICOM) viewer of each of cervical spine vertebrae C2 to C7, the method comprising: a user locating a pointing device on a start position of a selected image and moving the pointing device from the start position to a finish position in a continuous, single action along a margin of the vertebra and concomitantly, a processor drawing a continuous line between the start position and the finish position; repeating the step to provide a flexion trace and an extension trace of each of cervical spine vertebrae C2 to C7; superimposing the flexion trace on the extension trace; determining a MAR datum; and normalizing the MAR datum.

16. The method of claim 15, further comprising the user correcting an error in a trace.

17. The method of claim 16, wherein correcting includes the user selecting an erroneous segment of a trace with the pointing device and the processor removing the erroneous segment.

18. The method of claim 17, wherein correcting includes the user drawing a correct line with the pointing device and the processor replacing the erroneous segment.

* * * * *